United States Patent
Artsyukhovich

(10) Patent No.: US 8,348,430 B2
(45) Date of Patent: Jan. 8, 2013

(54) PHOTONIC LATTICE LEDS FOR OPHTHALMIC ILLUMINATION

(75) Inventor: Alexander Artsyukhovich, San Juan Capistrano, CA (US)

(73) Assignee: Alcon Research, Ltd., Fort Worth, TX (US)

( * ) Notice: Subject to any disclaimer, the term of this patent is extended or adjusted under 35 U.S.C. 154(b) by 207 days.

(21) Appl. No.: 12/903,262

(22) Filed: Oct. 13, 2010

(65) Prior Publication Data

US 2011/0149246 A1 Jun. 23, 2011

Related U.S. Application Data

(60) Provisional application No. 61/287,480, filed on Dec. 17, 2009, provisional application No. 61/287,425, filed on Dec. 17, 2009.

(51) Int. Cl.
*A61B 3/10* (2006.01)
*A61B 3/00* (2006.01)

(52) U.S. Cl. .................................. 351/221; 351/246
(58) Field of Classification Search ........... 351/200–246
See application file for complete search history.

(56) References Cited

U.S. PATENT DOCUMENTS

| | | |
|---|---|---|
| 3,026,449 A | 3/1962 | Rappaport |
| 4,222,375 A | 9/1980 | Martinez |
| 4,656,508 A | 4/1987 | Yokota |
| 4,870,952 A | 10/1989 | Martinez |
| 4,883,333 A | 11/1989 | Yanez |
| 4,884,133 A | 11/1989 | Kanno et al. |
| 5,086,378 A | 2/1992 | Prince |
| 5,301,090 A | 4/1994 | Hed |
| 5,420,768 A | 5/1995 | Kennedy |
| 5,465,170 A | 11/1995 | Arimoto |
| 5,526,190 A | 6/1996 | Hubble, III et al. |
| 5,591,160 A | 1/1997 | Reynard |
| 5,598,042 A | 1/1997 | Mix et al. |
| 5,634,711 A | 6/1997 | Kennedy et al. |
| 5,657,116 A | 8/1997 | Kohayakawa |
| 5,736,410 A | 4/1998 | Zarling et al. |
| 5,830,139 A | 11/1998 | Abreu |
| 5,859,693 A | 1/1999 | Dunne et al. |
| 5,997,163 A | 12/1999 | Brown |
| 6,000,813 A | 12/1999 | Krietzman |
| 6,015,403 A | 1/2000 | Jones |
| 6,036,683 A | 3/2000 | Jean et al. |
| 6,102,696 A | 8/2000 | Osterwalder et al. |
| 6,120,460 A | 9/2000 | Abreu |

(Continued)

FOREIGN PATENT DOCUMENTS

EP 1114608 B1 3/2003

(Continued)

OTHER PUBLICATIONS

Yasujima, H., et al; JP2006087764A; Publication Date Apr. 6, 2006; Abstract only—machine translation; espacenet.com.

(Continued)

*Primary Examiner* — Mohammed Hasan
(74) *Attorney, Agent, or Firm* — Keiko Ichiye

(57) ABSTRACT

Photonic lattice sources drive an optical fiber in an ophthalmic illuminator to illuminate the interior of an eye. To produce white light, an RGB combination of photonic lattice LEDs may be used. Alternatively, a bichromatic combination of photonic lattice LEDs produce white light.

17 Claims, 3 Drawing Sheets

U.S. PATENT DOCUMENTS

| | | | |
|---|---|---|---|
| 6,123,668 A | 9/2000 | Abreu | |
| D434,753 S | 12/2000 | Druckenmiller et al. | |
| 6,183,086 B1 | 2/2001 | Neubert | |
| 6,190,022 B1 | 2/2001 | Tocci et al. | |
| 6,211,626 B1 | 4/2001 | Lys et al. | |
| 6,213,943 B1 | 4/2001 | Abreu | |
| 6,217,188 B1 | 4/2001 | Wainwright et al. | |
| 6,226,126 B1 | 5/2001 | Conemac | |
| 6,268,613 B1 | 7/2001 | Cantu et al. | |
| 6,270,244 B1 | 8/2001 | Naum | |
| 6,272,269 B1 | 8/2001 | Naum | |
| 6,336,904 B1 | 1/2002 | Nikolchev | |
| 6,431,731 B1 | 8/2002 | Krietzman | |
| 6,436,035 B1 | 8/2002 | Toth et al. | |
| 6,459,844 B1 | 10/2002 | Pan | |
| 6,730,940 B1 | 5/2004 | Steranka et al. | |
| 6,786,628 B2 | 9/2004 | Steen et al. | |
| 6,893,258 B1 | 5/2005 | Kert | |
| 6,917,057 B2 | 7/2005 | Stokes et al. | |
| 6,960,872 B2 | 11/2005 | Beeson et al. | |
| 7,025,464 B2 | 4/2006 | Beeson et al. | |
| 7,063,436 B2 | 6/2006 | Steen et al. | |
| 7,229,202 B2 | 6/2007 | Sander | |
| 7,276,737 B2 | 10/2007 | Camras et al. | |
| 7,301,271 B2 | 11/2007 | Erchak et al. | |
| 7,325,957 B2 | 2/2008 | Morejon et al. | |
| 7,344,279 B2 | 3/2008 | Mueller et al. | |
| 7,349,163 B2 | 3/2008 | Angelini et al. | |
| 7,403,680 B2 | 7/2008 | Simbal | |
| 7,482,636 B2 | 1/2009 | Murayama et al. | |
| 7,494,228 B2 | 2/2009 | Harbers et al. | |
| 7,556,412 B2 | 7/2009 | Guillermo | |
| 7,561,329 B2 | 7/2009 | Zahniser et al. | |
| 7,682,027 B2 | 3/2010 | Buczek et al. | |
| 7,918,583 B2 | 4/2011 | Chakmakjian et al. | |
| 7,990,587 B2 | 8/2011 | Watanabe | |
| 2001/0052930 A1 | 12/2001 | Adair et al. | |
| 2002/0003928 A1 | 1/2002 | Bischel et al. | |
| 2002/0087149 A1 | 7/2002 | McCary | |
| 2002/0137984 A1 | 9/2002 | Chhibber et al. | |
| 2003/0112421 A1 | 6/2003 | Smith | |
| 2003/0132701 A1 | 7/2003 | Sato et al. | |
| 2003/0147254 A1 | 8/2003 | Yoneda et al. | |
| 2003/0169603 A1 | 9/2003 | Luloh et al. | |
| 2003/0223248 A1 | 12/2003 | Cronin et al. | |
| 2003/0223249 A1 | 12/2003 | Lee et al. | |
| 2004/0004846 A1 | 1/2004 | Steen et al. | |
| 2004/0090796 A1 | 5/2004 | Steen et al. | |
| 2004/0124429 A1 | 7/2004 | Stokes et al. | |
| 2004/0233655 A1 | 11/2004 | Zimmerman et al. | |
| 2005/0018309 A1 | 1/2005 | McGuire, Jr. et al. | |
| 2005/0024587 A1 | 2/2005 | Somani | |
| 2005/0047172 A1 | 3/2005 | Sander | |
| 2005/0063171 A1 | 3/2005 | Leitel et al. | |
| 2005/0099824 A1 | 5/2005 | Dowling et al. | |
| 2005/0110808 A1 | 5/2005 | Goldschmidt et al. | |
| 2005/0140270 A1 | 6/2005 | Henson et al. | |
| 2005/0190562 A1 | 9/2005 | Keuper et al. | |
| 2005/0243539 A1 | 11/2005 | Evans et al. | |
| 2005/0270775 A1 | 12/2005 | Harbers et al. | |
| 2006/0203468 A1 | 9/2006 | Beeson et al. | |
| 2006/0262272 A1 | 11/2006 | Anderson et al. | |
| 2007/0102033 A1 | 5/2007 | Petrocy | |
| 2007/0133211 A1 | 6/2007 | Yoneda et al. | |
| 2007/0213618 A1 | 9/2007 | Li et al. | |
| 2007/0219417 A1 | 9/2007 | Roberts et al. | |
| 2007/0273290 A1 | 11/2007 | Ashdown et al. | |
| 2007/0284597 A1 | 12/2007 | Nawashiro et al. | |
| 2007/0291491 A1 | 12/2007 | Li et al. | |
| 2008/0030984 A1 | 2/2008 | Harbers et al. | |
| 2008/0073616 A1 | 3/2008 | Dong et al. | |
| 2008/0112153 A1 | 5/2008 | Iwasaki et al. | |
| 2008/0144169 A1 | 6/2008 | Zahniser et al. | |
| 2008/0175002 A1 | 7/2008 | Papac et al. | |
| 2008/0208006 A1 | 8/2008 | Farr | |
| 2008/0246919 A1 | 10/2008 | Smith | |
| 2008/0246920 A1 * | 10/2008 | Buczek et al. | 351/221 |
| 2008/0262316 A1 | 10/2008 | Ajima et al. | |
| 2008/0291682 A1 | 11/2008 | Falicoff et al. | |
| 2009/0036955 A1 | 2/2009 | Han | |
| 2009/0054957 A1 | 2/2009 | Shanbaky | |
| 2009/0092750 A1 | 4/2009 | Yang et al. | |
| 2009/0095960 A1 | 4/2009 | Murayama | |
| 2009/0105698 A1 | 4/2009 | Hodel et al. | |
| 2009/0131823 A1 | 5/2009 | Andreyko et al. | |
| 2009/0154137 A1 | 6/2009 | Bierhuizen et al. | |
| 2009/0154192 A1 | 6/2009 | Krattiger | |
| 2009/0168395 A1 | 7/2009 | Mrakovich et al. | |
| 2009/0182313 A1 | 7/2009 | Auld | |
| 2009/0190371 A1 | 7/2009 | Root et al. | |
| 2009/0203966 A1 | 8/2009 | Mizuyoshi | |
| 2009/0219586 A1 | 9/2009 | Fujimoto et al. | |
| 2009/0227847 A1 | 9/2009 | Tepper et al. | |
| 2009/0267088 A1 | 10/2009 | Peng et al. | |
| 2010/0100006 A1 | 4/2010 | Xu et al. | |
| 2010/0127299 A1 | 5/2010 | Smith et al. | |
| 2010/0177280 A1 * | 7/2010 | Buczek et al. | 351/221 |
| 2010/0182569 A1 | 7/2010 | Artsyukhovich et al. | |
| 2010/0228089 A1 | 9/2010 | Hoffman et al. | |
| 2010/0317923 A1 | 12/2010 | Endo et al. | |
| 2011/0009752 A1 | 1/2011 | Chen et al. | |
| 2011/0037948 A1 | 2/2011 | Horvath et al. | |
| 2011/0037949 A1 | 2/2011 | Papac et al. | |
| 2011/0038174 A1 | 2/2011 | Papac et al. | |
| 2011/0122366 A1 | 5/2011 | Smith | |
| 2011/0149246 A1 | 6/2011 | Artsyukhovich | |
| 2011/0149591 A1 | 6/2011 | Smith | |
| 2011/0292343 A1 * | 12/2011 | Papac et al. | 351/221 |

FOREIGN PATENT DOCUMENTS

| | | |
|---|---|---|
| JP | 2006087764 A | 4/2006 |
| WO | 00/54655 A1 | 9/2000 |
| WO | 2008/133736 A2 | 11/2008 |

OTHER PUBLICATIONS

Liu, C.K., et al; "High Efficiency Silicon-Based High Power LED Package Integrated with Micro-Thermoelectric Device"; Microsystems Packaging, Assembly and Circuits Technology; pp. 29-33; 2007 Taipei Conference Paper; IMPACT 2007, worldwide web: www.ieee.org; DOI 10.1109/IMPACT.2007.4433562.

PCT/US2012/052200; International Search Report dated Oct. 26, 2012.

* cited by examiner

PHOTONIC LATTICE LEDS FOR OPHTHALMIC ILLUMINATION

This application claims priority to U.S. Provisional Application Ser. No. 61/287,480 filed on Dec. 17, 2009 and U.S. Provisional Application Ser. No. 61/287,245 filed on Dec. 17, 2009.

TECHNICAL FIELD

This application relates to illumination in ophthalmic procedures and more particularly to ophthalmic illumination with photonic lattice light emitting diodes (photonic lattice LEDs).

BACKGROUND

Ophthalmic illuminators allow a surgeon to illuminate the interior structure of the eye such as the vitreous and the retina during surgical procedures. An endoscopic ophthalmic illuminator (endo-illuminator) includes an optical fiber within the bore of a cannula. By driving a proximal end of the optical fiber with a suitable light source, light emitted from a distal end of the fiber illuminates the desired portion of the eye. Modern small-incision techniques require a relatively high-gauge cannula such as 20 gauge (0.0295 inch diameter) or even higher gauges such as 25 gauge. But the surgeons also want sufficient luminous power from the endo-illuminator to properly illuminate the surgical field within the eye.

These two goals—using a high-gauge cannula vs. achieving sufficient luminous power are at odds with one another as follows. Because the cannula holds the optical fiber in its bore, as the gauge of the cannula is increased, the thickness of the enclosed optical fiber will need to be decreased accordingly. This decrease in the optical fiber diameter reduces the fiber's etendue, which relates to the light gathering ability for the fiber as determined by a product of the fiber's diameter and the fiber's numerical aperture. In contrast, the etendue for an endo-illuminator light source such as a conventional light-emitting diode (LED) is relatively high. Under the law of conservation of etendue, light must be lost when a high-etendue source drives a low-etendue fiber. In other words, only that portion of light from the source subtended by the optical fiber's etendue will couple to the optical fiber. The remainder of the light from the source must be lost. This is not an issue when a highly luminous source such as a xenon, halogen, or high-intensity discharge (HID) bulb is used as the endo-illuminator source in that the fraction of the light output from such relatively powerful sources coupled to the fiber is of sufficient luminous power to satisfactorily illuminate the surgical field. But such conventional non-solid-state sources produce a relatively large amount of heat while consuming substantial power. In contrast, an LED source for an endo-illuminator is much cooler and consumes less power, making it more suitable for battery-powered applications. Moreover, an LED source would be safer as LEDs are less prone to burning out during surgical procedures as compared to conventional bulb sources. In addition, LEDs are less costly as compared to halogen or HID sources. Although LEDs thus make an attractive alternative to the conventional use of HID or halogen bulbs, their luminous power is typically less than a conventional bulb source. Thus, due to the relatively high etendue of a conventional LED and its relatively low luminous power, the conventional LED will not pass sufficient light energy into a low etendue optical fiber.

Accordingly, there is a need in the art for an improved ophthalmic illuminator that enjoys the advantages of an LED source yet provides sufficient luminous power to the surgical field within the eye.

SUMMARY

In accordance with a first aspect of the disclosure, an ophthalmic illuminator is provided that includes a red photonic lattice LED; a blue photonic lattice LED; a green photonic lattice LED; an optical combiner operable to combine light beams from the red, blue, and green photonic lattice LEDs into a single beam; a lens; and an optical fiber, wherein the lens is operable to focus the single beam onto a proximal end of the optical fiber.

In accordance with a second aspect of the invention, an ophthalmic illuminator is provided that includes a first photonic lattice LED; a second photonic lattice LED; an optical combiner operable to combine light beams from the first and second photonic lattice LEDs into a single beam; a lens; and an optical fiber, wherein the lens is operable to focus the single beam onto a proximal end of the optical fiber.

In accordance with a third aspect of the invention, a method of providing illumination to the interior of an eye is provided that includes providing a first photonic lattice LED and a second photonic lattice LED; driving the first and second photonic lattice LEDs with respective currents so that each LED produces a light beam; aligning the light beams from the first and second photonic lattice LEDs into a single light beam; focusing the single light beam onto a proximal end of an optical fiber; and transmitting light from a distal end of the optical fiber to illuminate the interior of the eye.

DETAILED DESCRIPTION

A class of light-emitting diodes (LEDs) known as photonic lattice LEDs are exploited to drive the optical fiber in an endo-illuminator. Because photonic lattice LEDs are relatively-low etendue sources, there is a high degree of efficiency when such a source drives the relatively-low etendue optical fibers necessitated by the high gauge cannulas desirable for an endo-illuminator. In this fashion, there is a sufficient degree of coupling of the light radiated by the photonic lattice LED into the endo-illuminator's optical fiber so as to illuminate the surgical field in the eye with an adequate level of lumens.

In contrast to a photonic lattice LED, a conventional LED emits light both normally and laterally with regard to the LED's surface. But the surface of a photonic lattice LED is patterned with sub-wavelength microstructures that are self-collimating such that the emission of the laterally-directed light is minimized or eliminated. The lattice-like arrangement of the microstructures in a photonic lattice LED directs photons normally from the LED surface and suppresses conventional lateral propagation. Thus, a photonic lattice LED is not only brighter than a comparable conventional LED but the self-collimated nature of its light emission simplifies its coupling to an optical system. An example photonic lattice LED is disclosed in U.S. Pat. No. 7,301,271, the contents of which are incorporated by reference in their entirety. Photonic lattice LEDs are commercially available from, for example, Luminous Devices, Inc.

Figure 1A:
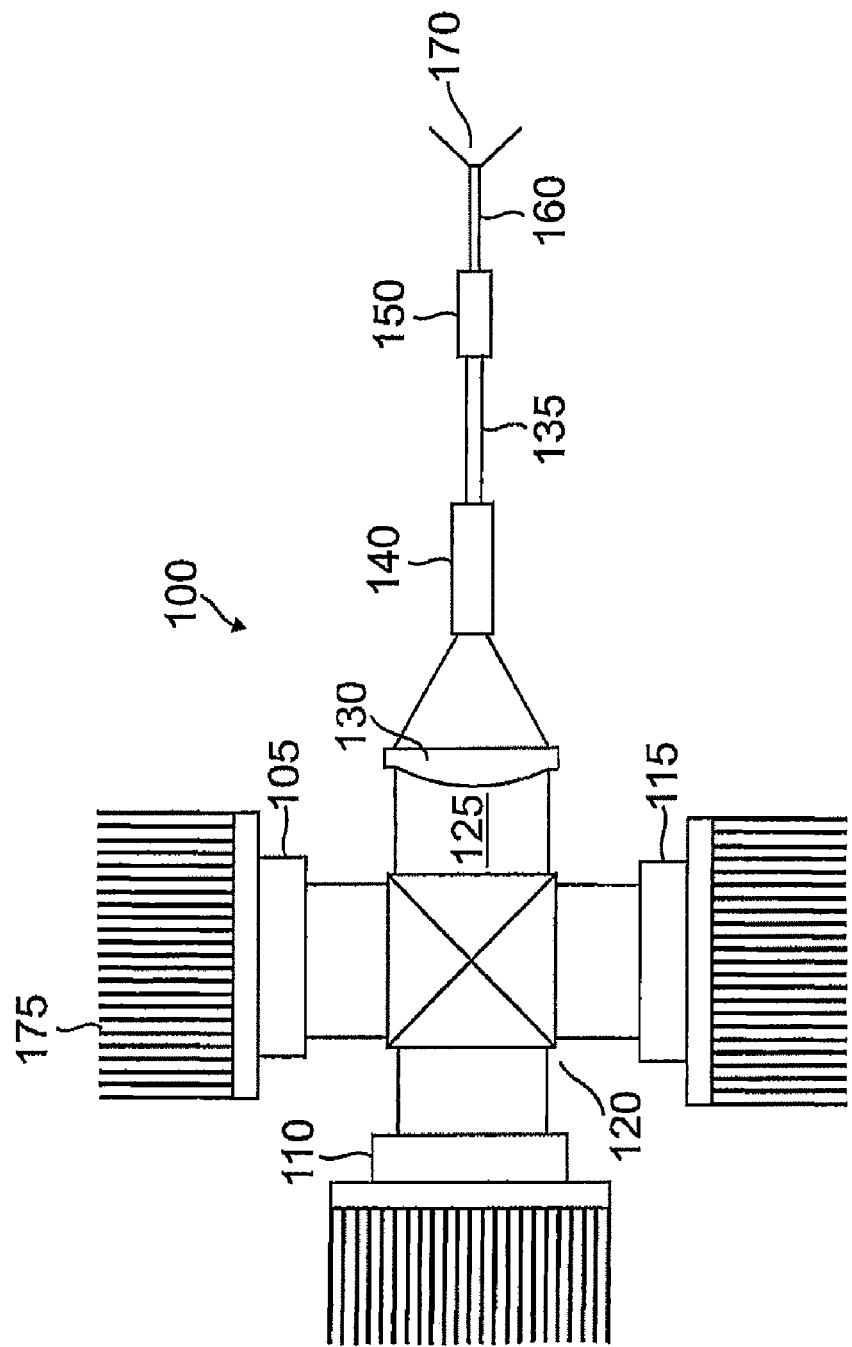
FIG. 1a is a diagram of an RGB photonic lattice LED ophthalmic illuminator.

The following discussion will be directed to an endo-illuminator using multiple photonic lattice LEDs of different colors to produce a white light illumination. However, it will be appreciated that the principles disclosed herein may readily be applied to construct a single white-light photonic lattice LED ophthalmic illuminator. Turning now to the drawings, a red, green, blue (RGB) ophthalmic illuminator 100 drives an optical fiber for endo-illumination as shown in FIG. 1a. A blue photonic lattice LED 105, a red photonic lattice LED 110, and a green photonic lattice LED 115 are aligned to properly drive an X prism 120. Because of the self-collimating nature of photonic lattice LEDs, collimators between LEDs 105, 110, and 115 and X prism 120 are not necessary. X prism 120 acts to align the collimated light beams provided by each photonic lattice LED into a single light beam 125. It will be appreciated that other types of optical combiners may be used to provide light beam 125 from the photonic lattice LEDs. A lens such as an aspheric lens 130 focuses light beam 125 onto a proximal end of an optical fiber 135 within a connector 140. Fiber 135 couples through a handpiece 150 (not drawn to scale) to a probe or cannula 160 to provide an illuminating emission 170 for illumination inside an eye. Cannula 160 may be formed using stainless steel or other suitable materials. Heat sinks 175 draw heat away from the photonic lattice LEDs during operation of ophthalmic illuminator 100.

A surgeon may wish to alter the composition of the light produced by ophthalmic illuminator 100 to better highlight certain features during surgery. For example, the surgeon may want a bluer tone during one procedure or a different tone during another procedure (or with respect to portions of the same procedure). To alter the color and perceived intensity of the light provided by the ophthalmic illuminator 100, the photonic lattice LEDs may be modulated as described in U.S. Pat. No. 7,286,146 titled "Method and System for LED Temporal Dithering to Achieve Multi-bit Color Resolution," which is hereby incorporated by reference in its entirety. In such a procedure, the actual frequency of light produced by the LEDs does not change but because of the low pass nature of human vision, the perceived color of the nominally-white light produced by illuminator 100 can be changed by sequentially pulsing the photonic lattice LEDs at a sufficiently high rate (e.g., greater than 1 kHz) to create a visual perception of a desired color of light. Generally, this can be accomplished through various techniques such as, for example, pulse width modulation, temporal dithering, and other suitable techniques. For example, a controller (not illustrated) could drive photonic lattice LEDs 105, 110, and 115 with a substantially constant current for particular periods of time. The shorter the period time that the substantially constant current is supplied to given one of the photonic lattice LEDs, the less brightness (i.e. perceived intensity) an observer would observe for the light being emitted the photonic lattice LEDs. Thus, by cycling between photonic lattice LEDs 105, 110, and 115 at different frequencies one can create the perception of different colors for illuminating beam 170. Alternatively current can be adjusted individually on each LED to alter light output and resulting color in the combined output.

Figure 1B:
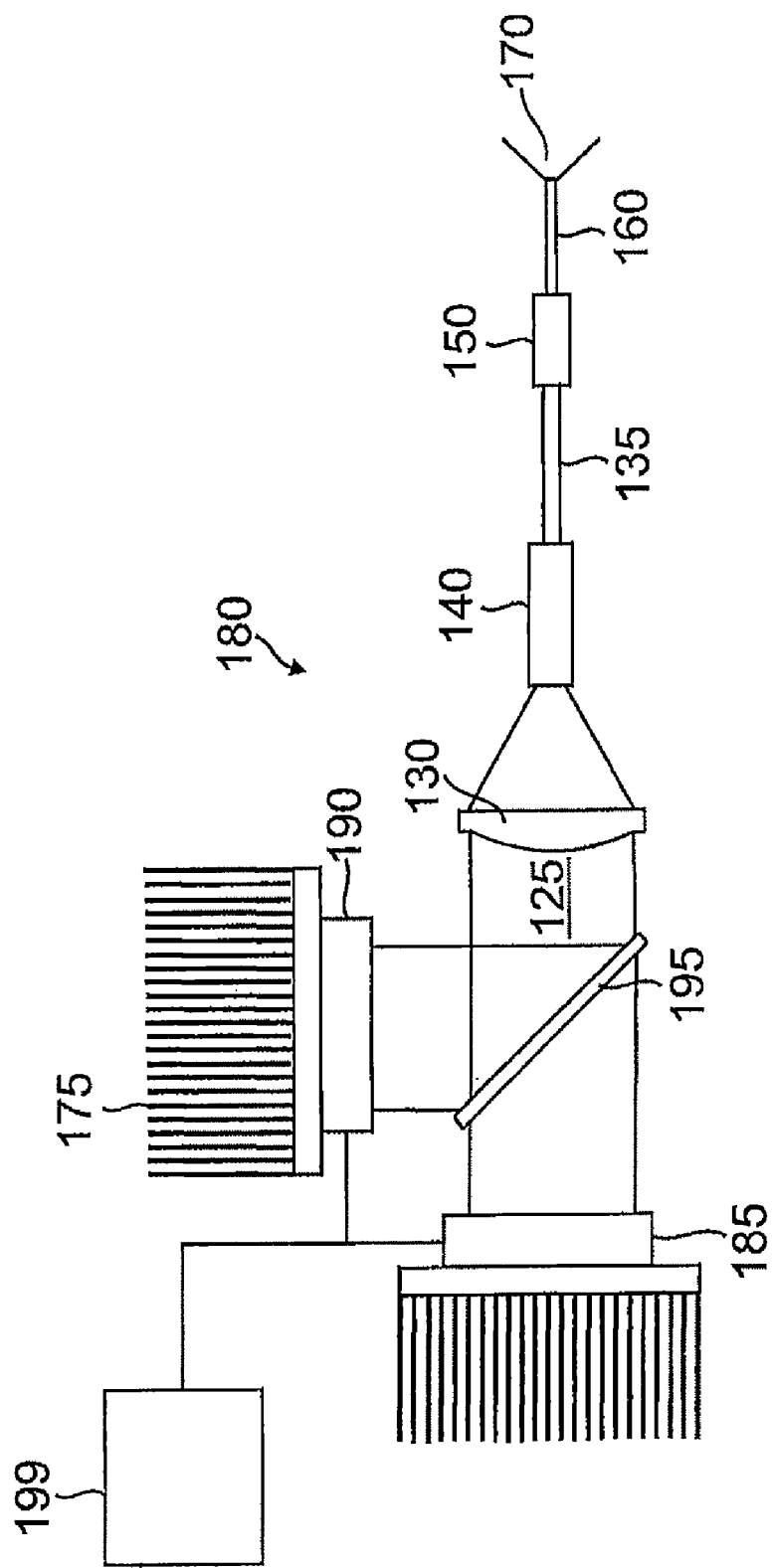
FIG. 1b is a diagram of a bi-chromatic photonic lattice LED ophthalmic illuminator.

To reduce the number of required LED sources, a single white photonic lattice LED could be used to replace the colored LEDs in illuminator 100. In a white LED embodiment, an optical combiner such as X prism 120 is of course unnecessary. Instead, lens 130 would be aligned with the white LED such that the remainder of a white LED ophthalmic illuminator would be as illustrated in FIG. 1 with respect to illuminator 100. However, white light photonic lattice LEDs are presently unavailable. Thus, to reduce the number of required LED sources with regard to illuminator 100, a bi-chromatic ophthalmic illuminator 180 is disclosed as illustrated in FIG. 1b. Illuminator 180 includes a first photonic lattice LED 185 and a second photonic lattice LED 190 that each mix through an optical combiner such as a dichroic mirror 195. Dichroic mirrors act as color filters in that they pass light of a selected narrow band of color while reflecting all other colors of light. Thus, for illuminator 180, dichroic mirror 195 is configured to pass light from LED 185 while reflecting light from LED 190. The result is a combined single light beam 125. The remaining components in FIG. 1b function as described with regard to illuminator 100 of FIG. 1a. LEDs 185 and 190 each produce a specific color of light as discussed further with regard to a chromaticity diagram 200 of FIG. 2.

Figure 2:
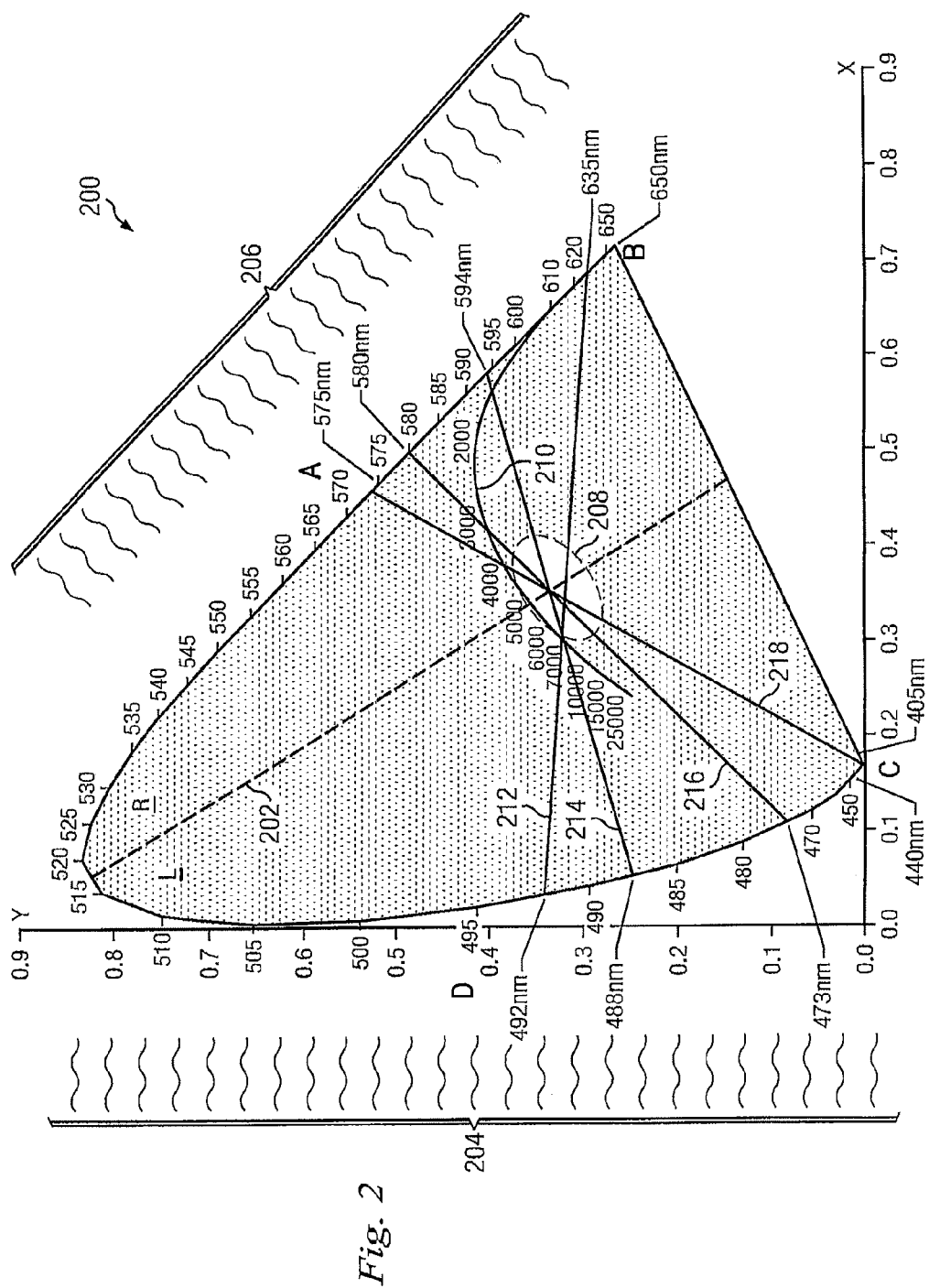
FIG. 2 is chromaticity diagram depicting a white light region that can be achieved by appropriate pairings of monochromatic sources such as the photonic lattice LEDs in the bi-chromatic ophthalmic illuminator of FIG. 1b.

FIG. 2 shows a chromaticity diagram 200, or graph, depicting a white light region that can be achieved by bi-chromatic ophthalmic illuminator 180 according to an embodiment of the present disclosure. For example, chromaticity diagram 200 can be a CIE 1931 chromaticity graph, a CIE 1976 chromaticity graph, or any other suitable chromaticity graph. Chromaticity diagram 200 generally represents the range of colors that are viewable by a human eye. More specifically, the diagram represents the range of colors that can be produced by a monochromatic light source such as photonic lattice LEDs 185 and 190 discussed above.

As shown, the chromaticity diagram 200 is divided by a dividing line 202 such that the diagram is divided into a left half L and a right half R. In that regard, the right and left halves of the chromaticity diagram represent the possible colors capable of being produced by photonic lattice LEDs. Thus, the chromaticity diagram 200 is divided into two halves such that the left half L represents a first photonic lattice LED 204 emitting a light having a wavelength less than approximately 518 nm and the right half R represent a second photonic lattice LED 206 emitting a light having a wavelength greater than approximately 518 nm.

A white region 208 is shown adjacent a black body curve 210. As shown, dividing line 202 divides white region 208. White region 208 represents a spectral region of white light capable of being produced by combining a monochromatic light source from each of the left and right halves of the chromaticity diagram 200. More specifically, white region 208 encompasses the different color temperatures of white light along or near black body curve 210 from the alignment of LEDs 204 and 206. Therefore, dividing line 202 defines a reference point through white region 208 that allows for the production of white light by mixing the wavelength of light emitted from the first monochromatic light source 204 from the left half L with the wavelength of light emitted from the second monochromatic light source 206 from the right half R.

Photonic lattice LEDs 204 and 206 are configured to produce light at a specific wavelength within the range of about 400 nm to about 700 nm. In other words, LEDs 204 and 206 each produce some unique color within the spectrum of visible light. In that regard, FIG. 2 shows that photonic lattice LED 204 emits a light having a wavelength of approximately less than 518 nm and photonic lattice LED 206 emits a light having a wavelength of approximately more than 518 nm.

As seen in FIG. 2, when LED 204 emits a light at a specified wavelength from the left half L and LED 206 emits a light at a specified wavelength from the right half R, the resultant light produced by the mixture can be defined as a specific point along a light color axis that extends between the two sources on the chromaticity diagram of FIG. 2. Although the specified wavelengths can be any arbitrary value, it has been found that an optimal effectiveness for producing white light is achieved when combining certain ranges of wavelengths. As shown in FIG. 2, a region CD of wavelengths (e.g. 495 nm-405 nm) and a region AB of wavelength (e.g. 575 nm-650 nm) represents the optimal regions of wavelengths to select for optimal effectiveness for producing white light using two monochromatic light sources such as LEDs 204 and 206. In other words, it is optimal when mixing LEDs sources 204 and 206 to produce white light to select LED 204 such that it emits a light having a wavelength falling within the region CD and to select LED 206 such that it emits a light having a wavelength falling within the region AB.

As shown in FIG. 2, should LED 204 be selected for operation at 492 nm and LED 206 selected for operation to 620 nm, the resulting perception of the combined light for such sources to the human eye will lie along a light color axis 212. If, however, LEDS 204 and 206 are selected for operation at other specific frequencies, other light axii will result such as light color axii 214, 216, and 218. Table 1 below shows the various combinations of light wavelengths being produced by sources 204 and 206 that define light color axii 212, 214, 216, and 218 that intersect white region 208 of the color spectrum shown in chromaticity graph 200.

TABLE 1

Light Axii Intersecting White Region

| Light Axis | Monochromatic Light Source 204 | Monochromatic Light Source 206 |
|---|---|---|
| 212 | 492 nm | 635 nm |
| 214 | 488 nm | 594 nm |
| 216 | 473 nm | 580 nm |
| 218 | 405 nm | 575 nm |

Although Table 1 above shows specific examples of combinations of wavelengths of light that produce light color axii that intersect white region 208, the table is to be considered for exemplary purposes only and not to be construed as any explicit or implicit limitation of possible combinations of wavelengths that can be used. Moreover, the combination of wavelengths presented in Table 1 includes wavelengths selected from regions AB and CD and this in no way implies a limitation of the possible ranges of wavelength combinable from either side of dividing line 202 of chromaticity graph 200 that can be used to define a light color axis that intersects white region 208. An example color assignment for the LED pairs would be yellow/violet or turquoise/red.

Referring again to FIG. 1b, if the relative intensity of LEDs 185 and 190 are modulated using a controller 199 through, for example the techniques discussed with regard to illuminator 100 of FIG. 1a, illuminator 180 will produce light 170 that is perceived to have a color lying on a point on color axis 212 within white region 208. By changing the modulation of LEDs 185 and 190, the perceived color will be changed from one point on color axis 212 to another. Further details of tuning bi-chromatic sources such as LEDs 185 and 190 to produce a desired color may be found in commonly-assigned U.S. Application 61/287,425, entitled "Bichromatic White Ophthalmic Illuminator," the contents of which are incorporated by reference herein in their entirety.

Embodiments described above illustrate but do not limit the invention. It should also be understood that numerous modifications and variations are possible in accordance with the principles of the present invention. Accordingly, the scope of the invention is defined only by the following claims.

I claim:

1. An ophthalmic illuminator, comprising:
   a red photonic lattice LED;
   a blue photonic lattice LED;
   a green photonic lattice LED;
   an optical combiner operable to combine light beams from the red, blue, and green photonic lattice LEDs into a single beam;
   a lens;
   an optical fiber, wherein the lens is operable to focus the single beam onto a proximal end of the optical fiber; and
   a controller operable to modulate the red, green, and blue photonic lattice LEDs to change a color of the single beam.

2. The ophthalmic illuminator of claim 1, wherein the optical combiner is an X-prism optical combiner.

3. The ophthalmic illuminator of claim 1, further comprising:
   a handpiece; and
   a probe extending from a distal end of the handpiece, wherein a distal portion of the optical fiber extends through the handpiece and into the probe.

4. The ophthalmic illuminator of claim 3, wherein the probe is a stainless steel probe.

5. The ophthalmic illuminator of claim 1, further comprising a plurality of heat sinks operable to sink heat from the red, green, and blue photonic lattice LEDs.

6. The ophthalmic illuminator of claim 1, wherein the lens is an aspheric lens.

7. An ophthalmic illuminator, comprising:
   a first photonic lattice LED;
   a second photonic lattice LED;
   an optical combiner operable to combine light beams from the first and second photonic lattice LEDs into a single beam;
   a lens;
   an optical fiber, wherein the lens is operable to focus the single beam onto a proximal end of the optical fiber; and
   a controller operable to modulate the first and second photonic lattice LEDs to change a color of the single beam.

8. The ophthalmic illuminator of claim 7, wherein the first photonic lattice LED produces a light beam having a first wavelength and the second photonic lattice LED produces a light beam having a second wavelength, and wherein the single beam is a white beam as a result of the first and second wavelengths.

9. The ophthalmic illuminator of claim 8, wherein the first wavelength corresponds to yellow light and the second wavelength corresponds to violet light.

10. The ophthalmic illuminator of claim 8, wherein the first wavelength corresponds to turquoise light and the second wavelength corresponds to red light.

11. The ophthalmic illuminator of claim 7, wherein the optical combiner is a dichroic mirror.

12. The ophthalmic illuminator of claim 7, wherein the lens is an aspheric lens.

13. The ophthalmic illuminator of claim 7, further comprising:
   a handpiece; and
   a probe extending from a distal end of the handpiece, wherein a distal portion of the optical fiber extends through the handpiece and into the probe.

14. A method of providing illumination to the interior of an eye, the method comprising:

provideing a first photonic lattice LED and a second photonic lattice LED;

driving the first and second photonic lattice LEDs with respective currents so that each LED produces a light beam combining the light beams from the first and second photonic lattice LEDs into a single light beam;

focusing the single light beam onto a proximal end of an optical fiber;

transmitting light from a distal end of the optical fiber to illuminate the interior of the eye; and modulating the respective currents to change a color of the single light beam.

15. The method of claim 14, wherein a first wavelength of light emitted by the first photonic lattice LED and a second wavelength of light emitted by the second photonic lattice LED define a light axis that intersects a white region of a chromaticity graph.

16. The method of claim 14, further comprising modulating the respective currents so that the color of the single light beam lies within the white region.

17. The method of claim 16, wherein the modulation comprises one of pulse width modulation and amplitude modulation.

* * * * *